United States Patent [19]

Sawanishi et al.

[11] Patent Number: 5,432,192
[45] Date of Patent: Jul. 11, 1995

[54] TRICYCLIC COMPOUNDS AND METHOD FOR TREATING ALLERGIC DISEASES

[75] Inventors: Hiroyuki Sawanishi, Kanazawa; Yasuo Ito, Katsuyama; Hideo Kato, Fukui; Eiichi Koshinaka, Katsuyama; Nobuo Ogawa, Katsuyama; Kouji Morikawa, Katsuyama, all of Japan

[73] Assignee: Hokuriku Seiyaku Co., Ltd., Japan

[21] Appl. No.: 122,603

[22] PCT Filed: Mar. 26, 1992

[86] PCT No.: PCT/JP92/00365
§ 371 Date: Oct. 1, 1993
§ 102(e) Date: Oct. 1, 1993

[87] PCT Pub. No.: WO92/17440
PCT Pub. Date: Oct. 15, 1992

[30] Foreign Application Priority Data

Apr. 5, 1991 [JP] Japan ................... 3-099775
May 21, 1991 [JP] Japan ................... 3-144107
Feb. 27, 1992 [JP] Japan ................... 4-075587

[51] Int. Cl.$^6$ ................... A61K 31/335; C07D 313/12
[52] U.S. Cl. ................... 514/450; 514/454; 514/510; 514/567; 549/354
[58] Field of Search ................... 549/354, 390; 560/38; 562/443; 514/450, 454, 510, 567

[56] References Cited

U.S. PATENT DOCUMENTS 3,991,103 11/1976 Barton et al. ................... 549/354
4,629,691 2/1986 Collins et al. ................... 562/442
5,332,661 7/1994 Adamczyk et al. ................... 435/7.93

OTHER PUBLICATIONS

Hubbard et al., J. of Pharmaceut. Sciences, 67 (11), pp. 1571–1578 (1978).

*Primary Examiner*—Bernard Dentz
*Attorney, Agent, or Firm*—Cushman, Darby & Cushman

[57] ABSTRACT

Tricyclic compounds represented by the following formula:

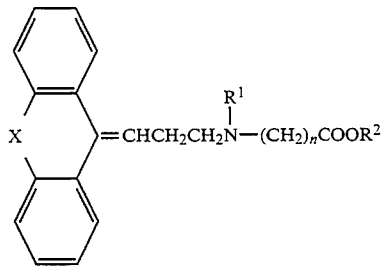

wherein
X represents —CH=CH—, —CH$_2$O—, or —O—;
R$^1$ represents a lower alkyl group,
R$^2$ represents a hydrogen atom or a lower alkyl group; and
n represents an integer of from 1 to 5, pharmacologically acceptable salts thereof, and a method for preparing the same. The present compounds have anti-allergic and anti-histaminic activities and reduced side effects, and are useful as anti-allergic agents and anti-histaminic agents.

7 Claims, No Drawings

TRICYCLIC COMPOUNDS AND METHOD FOR TREATING ALLERGIC DISEASES

This application is a 371 of PCT/JP92/00365 filed Mar. 26, 1992.

TECHNICAL FIELD

The present invention relates to novel tricyclic compounds which are useful as anti-histaminic agents and anti-allergic agents. The present invention also relates to processes for preparing said compounds and uses thereof.

BACKGROUND ART

As examples of therapeutic compounds having a tricyclic nucleus structurally similar to the compound of the present invention, Cyclobenzaprine (The Merck Index, 11th edition, 2719) useful as a muscle relax ant represented by the following formula (II):

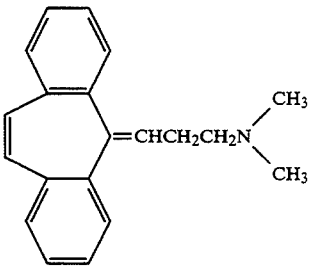

and Doxepin (The Merck Index, 11th edition, 3425) useful as an antidepressant and an antipruritic agent represented by the following formula (III):

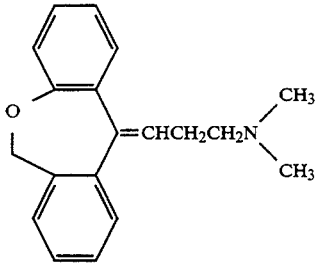

are known.

However, Cyclobenzaprine is known to cause adverse reactions such as sleepiness, dizziness, fatigue, thirst, nausea, constipation, and dyspepsia. Doxepin also induces adverse reactions such as sleepiness, thirst, and constipations. These adverse reactions are caused because Cyclobenzaprine or Doxepin have various pharmacological activities such as an activity on central nervous system and an anti-acetylcholinergic activity in addition to their principal activities, i.e., muscle relaxing, anti-depressing activities and anti-histaminic activities.

Accordingly, an object of the present invention is to provide a medicament having an excellent selectivity of increased desired principal activities and reduced side effects by separating various pharmacological activities induced by medicaments such as Cyclobenzaprine and Doxepin.

The inventors of the present invention conducted various studies to achieve the foregoing object and found that the object can be achieved by providing novel tricyclic compounds of the present invention. The inventors also found that the novel tricyclic compounds of the present invention have potent anti-histaminic and anti-allergic activities, and that they are useful as medicaments having excellent selectivities and reduced side effects caused by their anti-acetylcholinergic activity and the like. The present invention was achieved on the basis of these findings.

DISCLOSURE OF THE INVENTION

According to the present invention, novel tricyclic compounds and their pharmacologically acceptable salts are provided which are represented by the following formula (I):

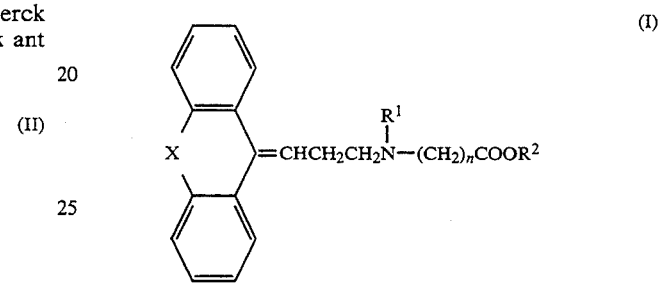

wherein
X represents —CH=CH—, —CH$_2$O—, or —O—;
R$^1$ represents a lower alkyl group,
R$^2$ represents a hydrogen atom or a lower alkyl group; and
n represents an integer of from 1 to 5.

According to another embodiment of the present invention, there are provided a process for preparing said compounds, and an anti-histaminic agent and an anti-allergic agent comprising an effective amount of said compound.

BEST MODE FOR CARRYING OUT THE INVENTION

In the above-described formula (I) according to the present invention, the lower alkyl group represented by R$^1$ and R$^2$ may be, for example, methyl, ethyl, n-propyl, isopropyl, n-butyl, isobutyl, sec-butyl, or tert-butyl.

Preferred compounds of the present invention include the following compounds:

(1) ethyl [N-[3-(5H-dibenzo[a,d]cyclohepten-5-ylidene)propyl]-N-methylamino]acetate;

(2) ethyl 3-[N-[3-(5H-dibenzo[a,d]cyclohepten-5-ylidene)propyl]-N-methylamino]propionate;

(3) ethyl 4-[N-[3-(5H-dibenzo[a,d]cyclohepten-5-ylidene)propyl]-N-methylamino]butyrate;

(4) ethyl 5-[N-[3-(5H-dibenzo[a,d]cyclohepten-5-ylidene)propyl]-N-methylamino]valerate;

(5) ethyl 6-[N-[3-(5H-dibenzo[a,d]cyclohepten-5-ylidene)propyl]-N-methylamino]hexanoate;

(6) [N-[3-(5H-dibenzo[a,d]cyclohepten-5-ylidene)propyl]-N-methylamino]acetic acid;

(7) 3-[N-[3-(5H-dibenzo[a,d]cyclohepten-5-ylidene)propyl]-N-methylamino]propionic acid;

(8) 4-[N-[3-(5H-dibenzo[a,d]cyclohepten-5-ylidene)propyl]-N-methylamino]butyric acid;

(9) 5-[N-[3-(5H-dibenzo[a,d]cyclohepten-5-ylidene)propyl]-N-methylamino]valeric acid;

(10) 6-[N-[3-(5H-dibenzo[a,d]cyclohepten-5-ylidene)-propyl]-N-methylamino]hexanoic acid;
(11) ethyl [N-3-(dibenz[b,e]oxepin-11(6H)-ylidene)-propyl]-N-methylamino]acetate;
(12) ethyl (E)-[N-[3-(dibenz[b,e]oxepin-11(6H)-ylidene)propyl]-N-methylamino]acetate;
(13) ethyl (Z)-[N-[3-(dibenz[b,e]oxepin-11(6H)-ylidene)propyl]-N-methylamino]acetate;
(14) ethyl 3-[N-[3-(dibenz[b,e]oxepin-11(6H)-ylidene)propyl]-N-methylamino]propionate;
(15) ethyl (E)-3-[N-[3-(dibenz[b,e]oxepin-11(6H)-ylidene)propyl]-N-methylamino]propionate;
(16) ethyl (Z)-3-[N-[3-(dibenz[b,e]oxepin-11(6H)-ylidene)propyl]-N-methylamino]propionate;
(17) ethyl 4-[N-[3-(dibenz[b,e]oxepin-11(6H)-ylidene)propyl]-N-methylamino]butyrate;
(18) ethyl (E)-4-[N-[3-(dibenz[b,e]oxepin-11(6H)-ylidene)propyl]-N-methylamino]butyrate;
(19) ethyl (Z)-4-[N-[3-(dibenz[b,e]oxepin-11(6H)-ylidene)propyl]-N-methylamino]butyrate;
(20) ethyl 5-[N-[3-(dibenz[b,e]oxepin-11(6H)-ylidene)propyl]-N-methylamino]valerate;
(21) ethyl (E)-5-[N-[3-(dibenz[b,e]oxepin-11(6H)-ylidene)propyl]-N-methylamino]valerate;
(22) ethyl (Z)-5-[N-[3-(dibenz[b,e]oxepin-11(6H)-ylidene)propyl]-N-methylamino]valerate;
(23) ethyl 6-[N-[3-(dibenz[b,e]oxepin-11(6H)-ylidene)propyl]-N-methylamino]hexanoate;
(24) ethyl (E)-6-[N-[3-(dibenz[b,e]oxepin-11(6H)-ylidene)propyl]-N-methylamino]hexanoate;
(25) ethyl (Z)-6-[N-[3-(dibenz[b,e]oxepin-11(6H)-ylidene)propyl]-N-methylamino]hexanoate;
(26) [N-[3-(dibenz[b,e]oxepin-11(6H)-ylidene)-propyl]-N-methylamino]acetic acid;
(27) (E)-[N-[3-(dibenz[b,e]oxepin-11(6H)-ylidene)-propyl]-N-methylamino]acetic acid;
(28) (Z)-[N-[3-(dibenz[b,e]oxepin-11(6H)-ylidene)-propyl]-N-methylamino]acetic acid;
(29) 3-[N-[3-(dibenz[b,e]oxepin-11(6H)-ylidene)-propyl]-N-methylamino]propionic acid;
(30) (E)-3-[N-[3-(dibenz[b,e]oxepin-11(6H)-ylidene)-propyl]-N-methylamino]propionic acid;
(31) (Z)-3-[N-[3-(dibenz[b,e]oxepin-11(6H)-ylidene)-propyl]-N-methylamino]propionic acid;
(32) 4-[N-[3-(dibenz[b,e]oxepin-11(6H)-ylidene)-propyl]-N-methylamino]butyric acid;
(33) (E)-4-[N-[3-(dibenz[b,e]oxepin-11(6H)-ylidene)-propyl]-N-methylamino]butyric acid;
(34) (Z)-4-[N-[3-(dibenz[b,e]oxepin-11(6H)-ylidene)-propyl]-N-methylamino]butyric acid;
(35) 5-[N-[3-(dibenz[b,e]oxepin-11(6H)-ylidene)-propyl]-N-methylamino]valeric acid;
(36) (E)-5-[N-[3-(dibenz[b,e]oxepin-11(6H)-ylidene)-propyl]-N-methylamino]valeric acid;
(37) (Z)-5-[N-[3-(dibenz[b,e]oxepin-11(6H)-ylidene)-propyl]-N-methylamino]valeric acid;
(38) 6-[N-[3-(dibenz[b,e]oxepin-11(6H)-ylidene)-propyl]-N-methylamino]hexanoic acid;
(39) (E)-6-[N-[3-(dibenz[b,e]oxepin-11(6H)-ylidene)-propyl]-N-methylamino]hexanoic acid;
(40) (Z)-6-[N-[3-(dibenz[b,e]oxepin-11(6H)-ylidene)-propyl]-N-methylamino]hexanoic acid;
(41) ethyl [N-[3-(9H-xanthen-9-ylidene)propyl]-N-methylamino]acetate;
(42) ethyl 3-[N-methyl-N-[3-(9H-xanthen-9-ylidene)propyl]amino]propionate;
(43) ethyl 4-[N-methyl-N-[3-(9H-xanthen-9-ylidene)propyl]amino]butyrate;
(44) ethyl 5-[N-methyl-N-[3-(9H-xanthen-9-ylidene)propyl]amino]valerate;
(45) ethyl 6-[N-methyl-N-[3-(9H-xanthen-9-ylidene)propyl]amino]hexanoate;
(46) [N-methyl-N-[3-(9H-xanthen-9-ylidene)propyl]amino]acetic acid;
(47) 3-[N-methyl-N-[3-(9H-xanthen-9-ylidene)propyl]amino]propionic acid;
(48) 4-[N-methyl-N-[3-(9H-xanthen-9-ylidene)propyl]amino]butyric acid;
(49) 5-[N-methyl-N-[3-(9H-xanthen-9-ylidene)propyl]amino]valeric acid; and
(50) 6-[N-methyl-N-[3-(9H-xanthen-9-ylidene)propyl]amino]hexanoic acid.

The compound of the present invention represented by the above formula (I) may optionally be converted to pharmacologically acceptable salts. Alternatively, the compounds prepared as their salts may be freed to prepare free compounds.

The pharmacologically acceptable salts of the compounds of the present invention represented by the above formula (I) include acid-addition salts and alkali-addition salts. Examples of the acid-addition salts include, for example, salts of inorganic acids such as hydrochloride, hydrobromide, sulfate, nitrate, and phosphate, and salts of organic acids such as acetate, maleate, fumarate, malate, citrate, oxalate, lactate, and tartrate. Examples of the alkali-addition salts include, for example, metal salts such as sodium salt, potassium salt, and calcium salt, and organic base salts such as ammonium salt, methylamine salt, ethylamine salt, dimethylamine salt, triethylamine salt, ethanolamine salt, piperidine salt, and piperazine salt.

The compound of the present invention represented by the above formula (I) may optionally exist in a form of a stereoisomer. The stereoisomers and the mixture thereof fall within the scope of the present invention.

According to an embodiment of the present invention, the tricyclic compound represented by the above-described formula (I) can be prepared in a manner described below. A process for preparing the compound of the present invention comprises the following steps:

(a) reacting a compound represented by the following formula (IV):

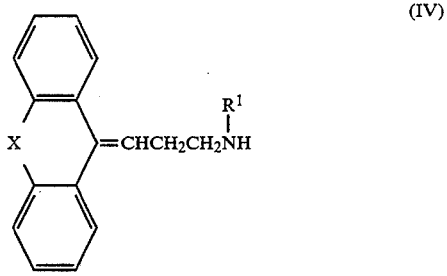

wherein

X and $R^1$ are the same as those defined above, with a compound represented by the following formula (V):

Y—$(CH_2)_n$ $COOR^2$ or $CH_2$=$CHCOOR^2$ (V)

wherein $R^2$ and n are the same as those defined above, and

Y represents a halogen atom, in a solvent or without a solvent in the presence or absence of a base as a dehydrohalogenating agent; and (b) hydrolysing the product using an acid or a base in a solvent if desired.

For the alkylation reaction of the process of the present invention, any solvent may be used insofar as it does not affect the reaction. Examples of such solvents include, for example, benzene, toluene, tetrahydrofuran, dioxane, acetone, acetonitrile, methanol, ethanol, isopropanol, n-butanol, dimethyl sulfoxide, and N,N-dimethylformamide. The bases used as a dehydrohalogenating agent may be, for example, potassium carbonate, sodium carbonate, pyridine, or triethylamine. The reaction may be carried out at from 0° C. to 200° C.

Examples of the acids used in the hydrolysis reaction include, for example, hydrochloric acid and sulfuric acid, and examples of the bases include, for example, sodium hydroxide, potassium hydroxide, potassium carbonate, sodium carbonate, and sodium hydrogen carbonate. As the reaction solvent, water, methanol, ethanol, acetone, or tetrahydrofuran may be used. The reaction may be carried out at from 0° C. to 100° C.

Methods for preparing the compounds represented by the above-described formula (IV) which are used as starting materials are specifically disclosed in Reference Examples. Some of these compounds are known to the public which are disclosed in, for example, Collect. Czech. Chem. Commun., Vol. 32, 2826–2839; Belgian patent publication No. 645,877; and Japanese patent laid open publication No. (Hei)3-500053.

According to still further embodiment of the present invention, a pharmaceutical composition is provided which comprises the tricyclic compound of the present invention or a pharmacologically acceptable salt thereof as an effective ingredient. The pharmaceutical composition is useful as an anti-allergic agent and an anti-histaminic agent.

The pharmaceutical composition of the present invention useful as an anti-allergic agent and an anti-histaminic agent may be administered orally or parenterally to a patient. Examples of the pharmaceutical composition suitable for oral administration include, for example, tablet, capsule, powder, subtilized granule, granule, solution, or syrup. Examples of the pharmaceutical composition suitable for parenteral administration include, for example, injection, suppository, inhalant, eye drop, nasal drop, ointment, or cataplasm. The pharmaceutical composition of the present invention may be prepared by adding pharmacologically and pharmaceutically acceptable additives. Examples of the pharmacologically and pharmaceutically acceptable additives include, for example, excipients, disintegrants or disintegrators, binders, lubricants, coating agents, dyes, diluents, bases, solubilizing agents or solubilizer, isotonic agents, pH adjusting agents, stabilizers, propellants, and adhesives.

For the pharmaceutical composition suitable for oral administration, transdermal administration, or transmucosal administration, pharmaceutical additives such as an excipient such as, for example, glucose, lactose, D-mannitol, starch, or crystalline cellulose; a disintegrant or a disintergrator such as, for example, carboxymethylcellulose, starch, or calcium carboxymethylcellulose; a binder such as, for example, hydroxypropylcellulose, hydroxypropylmethylcellulose, polyvinylpyrrolidone, or gelatin; a lubricant such as, for example, magnesium stearate or talc; a coating agent such as, for example, hydroxypropylmethylcellulose, sucrose, polyethylene glycol, or titanium oxide; a base such as, for example, vaseline, liquid paraffin, polyethyleneglycol, gelatin, kaolin, glycerin, purified water, or hard fat; a propellant such as, for example, flon, diethyl ether, or compressed gas; an adhesive such as, for example, sodium polyacrylate, polyvinyl alcohol, methylcellulose, polyisobutylene, or polybutene; and a cloth such as, for example, cotton cloth or plastic sheet may be added. For the pharmaceutical composition suitable for injection, pharmaceutical additives such as a solubilizing agent or a solubilizer such as, for example, distilled water for injection, physiological saline, or propylene glycol which can constitute an aqueous injection or a composition for preparing an injection before use; an isotonicity agent such as, for example, glucose, sodium chloride, D-mannitol, Or glycerin; a pH adjusting agent such as, for example, an inorganic acid, an organic acid, an inorganic base, or an organic base may be added.

The dose of the pharmaceutical composition of the present invention for a patient may generally be from about 1 to 500 mg per day for oral administration to an adult patient. However, the dose may be increased or decreased depending on the age or conditions of the patient.

Anti-histaminic, anti-allergic, and anti-acetylcholinergic effects of the compounds of the present invention will be demonstrated by way of experiments described below. Cyclobenzaprine (II) and Doxepin (III) were used as reference compounds.

EXPERIMENT 1

Anti-histaminic Effect

The ileum was isolated from male Hartley guinea-pigs (5 to 8 weeks of age). The preparation was suspended in a bath containing Locke-Ringer nutritional solution (NaCl: 154 mM, KCl: 5.6 mM, $CaCl_2 \cdot 2H_2O$: 2.2 mM, $MgCl_2 \cdot 6H_2O$: 2.1 mM, $NaHCO_3$: 5.9 mM, glucose: 2.8 mM) bubbled with 95% $O_2$+5% $CO_2$ mixed gas at 28° C., and then 0.5 g weight was loaded and tention through isotonic transducer was recorded using a recorder. Histamine was cumulatively applied 3 times at intervals of 40 minutes, and the dose-response curve of the third experiment, for which a test drug was applied 30 minutes before the experiment, was compared with the result of the second experiment as a reference. Dissociation constants $K_B$ (M) of antagonists were calculated according to the method of Furchgott. From the results shown in Table 1, it is apparent that the compounds of the present invention have excellent anti-histaminic activities.

TABLE 1

| | Anti-histaminic effect | | |
|---|---|---|---|
| Test compound | $-\text{Log } K_B$ | Test compound | $-\text{Log } K_B$ |
| Example 14 | 8.16 | Example 19 | 7.81 |
| Example 15 | 8.37 | Example 20 | 8.51 |
| Example 16 | 7.50 | Example 21 | 8.46 |
| Example 17 | 8.21 | Example 22 | 8.36 |
| Example 18 | 7.92 | Example 23 | 8.11 |

EXPERIMENT 2

Anti-allergic Effect (Inhibitory Effect on PCA Reaction)

Anti-allergic effects of the compounds of the present invention was estimated according to the method of Makino et al. (Japanese J. Pharmacology, 52, 87–94, 1990). 0.1 ml of anti-dinitrophenylated ascaris extract (DNP-As) rat IgE serum was injected intracutaneously to the back of male Wistar rats (6 weeks of age). After 48 hours, a solution of 1% Evans blue in physiological saline containing 1 mg of an antigen (DNP-As) was administered from caudal vein. After 30 minutes, the animals were exsanguinated and dyes in blue spots were extracted with 1N KOH, and then the amounts of the dyes were measured by absorbance at 620 nm. After the passively sensitized rats described above were fasted for 16 to 18 hours, 1 mg/kg of each test compound was administered orally to the rats, and then the rats were challenged with antigen after one hour. The amounts of dyes in the test animals were compared with those of the control to obtain the inhibition rate (%) of PCA reaction. From the results shown in Table 2, it is clearly demonstrated that the compounds of the present invention have excellent anti-allergic activities.

TABLE 2

| Anti-allergic effect (Inhibitory effect on PCA reaction) | | | |
|---|---|---|---|
| Test compound | Inhibition rate (%) | Test compound | Inhibition rate (%) |
| Example 14 | 72 | Example 22 | 62 |
| Example 17 | 72 | cyclobenzaprine | 14 |
| Example 18 | 50 | doxepin | 21 |
| Example 20 | 69 | | |

EXPERIMENT 3

Anti-acetylcholinergic Effect

The ileum was isolated from male Hartley guinea-pigs (5 to 8 weeks of age). The preparation was suspended in a bath containing Locke-Ringer nutritional solution (NaCl: 154 mM, KCl: 5.6 mM, $CaCl_2.H_2O$: 2.2 mM, $MgCl_2. 6H_2O$: 2.1 mM, $NaHCO_3$: 5.9 mM, glucose: 2.8 mM) bubbled with 95% $O_2$+5% $CO_2$ mixed gas at 28° C., and then 0.5 g weight was loaded and tention through isotonic transducer was recorded using a recorder. Acetylcholine was cumulatively applied 3 times at intervals of 40 minutes, and the dose-response curve of the third experiment, for which a test drug was applied 30 minutes before the experiment, was compared with the result of the second experiment as a reference. Dissociation constants $K_B$ (M) of antagonists were calculated according to the method of Furchgott. From the results shown in Table 3, it is apparent that the compounds of the present invention have almost no anti-acetylcholinergic activities.

TABLE 3

| Anti-acetylcholinergic effect | | | |
|---|---|---|---|
| Test compound | $-Log K_B$ | Test compound | $-Log K_B$ |
| Example 14 | 4.82 | Example 20 | 5.15 |
| Example 15 | 5.59 | Example 21 | 5.14 |
| Example 16 | 4.90 | Example 22 | 5.00 |
| Example 17 | 6.04 | Example 23 | 5.50 |
| Example 18 | 6.26 | cyclobenzaprine | 8.12 |
| Example 19 | 4.31 | doxepin | 7.23 |

From the experimental results set out above, it is apparent that the compounds of the present invention exhibit excellent anti-histaminic and anti-allergic effects, and that they have reduced undesirable side effects such as thirst and dysuria which are caused by anti-acetylcholinergic activity. It will be readily apparent to one of ordinary skill in the art that the compounds of the present invention are useful as anti-histaminic and anti-allergic agents having excellent selectivity.

The present invention will be hereinafter explained by way of examples. However, the present invention will not be limited to these examples.

REFERENCE EXAMPLE 1

Ethyl [N-[3-(Dibenz[b,e]oxepin-11(6H)-ylidene)propyl]-N-methylamino]formate

To a solution of 20.0 g of 11-[3-(dimethylamino)-propylidene]-6, 11-dihydrobenz[b,e]oxepin hydrochloride in 200 ml of chloroform, 50 ml of saturated aqueous sodium hydrogen carbonate was added under stirring. The chloroform layer was separated, washed with water, dried, and then the solvent was removed by distillation. After 100 ml of toluene was added to the residue, 18 ml of ethyl chloroformate was added dropwise with heating at 80° C. and then the mixture was refluxed for 6 hours. Ice water was added to the reaction mixture and the mixture was extracted with benzene. The organic layer was washed with water and dried, and then the solvent was removed by distillation. The residue was purified by column chromatography on silica gel [n-hexane-ethyl acetate (3:1)] to give 15.0 g of pale yellow viscous liquid.

Mass spectrum m/z: 337 (M+)

IR spectrum $v$ (liq) cm$^{-1}$: 1700 (COO)

NMR spectrum $\delta$ ($CDCl_3$) ppm: 1.16(3H,t,J=7.0Hz), 2.39(2H,q,J=7.0Hz), 2.74(3H,s), 3.37(2H,q,J=7.0Hz), 4.07(2H,q,J=7.0Hz), 5.20(2H,br-s), 5.98(1H,t,J=7.0Hz), 6.66–7.43(8H,m)

The compounds of Reference Example 2 and 3 were prepared in the same manner as described in Reference Example 1.

REFERENCE EXAMPLE 2

Ethyl [N-[3-(5H-Dibenzo[a,d]cyclohepten-5-ylidene)propyl-N-methylamino]formate

Appearance: colorless viscous liquid

Mass spectrum m/z: 333 (M+)

IR spectrum $v$ (liq) cm$^{-1}$: 1702 (COO)

NMR spectrum $\delta$ ($CDCl_3$) ppm: 1.13(3H,t,J=7.0Hz), 2.28(2H,q,J=7.0Hz), 2.72(3H,s), 3.27(2H,q,J=7.0Hz), 4.05(2H,q,J=7.0Hz), 5.48(1H,t, J=7.0Hz), 6.82(2H,s), 7.10–7.60(8H,m)

REFERENCE EXAMPLE 3

Ethyl [N-Methyl-N-[3-(9H-xanthen-9-ylidene)propyl]amino]-formate

Appearance: pale yellow oil

IR spectrum $v$ (liq) cm$^{-1}$: 1704

Mass spectrum m/z: 323 (M+)

NMR spectrum $\delta$ ($CDCl_3$) ppm: 1.24(3H,t,J=7.0Hz), 2.78(3H,br-s), 2.83–3.00(2H,m), 3.37–3.55(2H,m), 4.13(2H,q,J=7.0Hz), 5.73–5.90(1H,m 7.00–7.20(4H,m), 7.20–7.37(2H,m), 7.47–7.60(2H,m)

REFERENCE EXAMPLE 4

11-[3-(Methylamino)propylidene]-6,11-dihydrodibenz[b,e] oxepin Hydrochloride

A mixture of 10.1 g of ethyl [N-[3-(dibenz[b,e]oxepin-11(6H)-ylidene)propyl]-N-methylamino]formate, 8.42 g of potassium hydroxide, and 50 ml of n-butanol was refluxed for 3 hours. Ice-water was added to the reaction mixture, and the mixture was extracted with chloroform. The organic layer was washed with water and dried, and then the solvent was removed by distillation. The residue was purified by column chromatography on silica gel [chloroform-methanol (10:1)] and then the result was converted to hydrochloride by an ordinary method. Recrystallization from a mixture of methylene chloride and benzene gave 4.53 g of colorless crystals, mp 224°–227° C.

Analysis for $C_{18}H_{19}NO \cdot HCl$ Calculated C, 71.63; H, 6.68; N, 4.64 Found C, 71.74; H, 6.64; N, 4.56

The present compound was a mixture of stereo-isomers (E, Z) and the ratio of E-isomer (retention time: 22 min.) and Z-isomer (retention time: 17 min.) was about 70:30 as measured under HPLC conditions set out below.

Column: ULTRON ES-OVM (4.6 mm $\phi \times$ 150 mm)
Mobile phase: 20 mM $KH_2PO_4$ buffer (pH 4.0)—EtOH (7:1)
Flow rate: 0.6 ml / min.
Detection: Ultraviolet Spectrometer (225 nm)

The mixture obtained above was twice recrystallized from isopropanol to give (E)-11-[3-[(methylamino)-propylidene]-6,11-dihydrodibenz[b,e] oxepin hydrochloride.

NMR spectrum $\delta$ (DMSO-$d_6$) ppm: 2.38–2.54(2H,m), 2.91–3.07(2H,m), 3.21(3H,s), 5.21(2H,br-s), 6.02(1H,t,J=7.5Hz), 6.72(1H,dd,J=7.5, 1.0Hz), 6.90(1H,td,J=7.5,1.0Hz), 7.15(1H,td,J=7.5,1.0Hz), 7.27(1H, dd,J=7.5,1.0Hz), 7.31–7.52(4H,m), 8.74(2H,br-s) Purity: 97% (E-isomer:Z-isomer=97:3; HPLC analysis)

The compounds of Reference Example 5 and 6 were prepared in the same manner as described in Reference Example 4.

REFERENCE EXAMPLE 5

5-[3-(Methylamino)propylidene]-5H-dibenzo[a,d]cycloheptene

Appearance: colorless viscous liquid
Mass spectrum m/z: 261 (M+)
NMR spectrum $\delta$ (CDCl$_3$) ppm: 1.56(1H,s), 2.07–2.88(4H,m), 2.30 (3H,s), 5.53(1H,t,J=7.0Hz), 6.87(2H,s), 7.11–7.60(8H,m)

REFERENCE EXAMPLE 6

9-[3-(Methylamino)propylidene]-9H-xanthene Hydrochloride

Appearance: pale yellow crystals (iso-PrOH) mp 183°–185.5° C.
Analysis for $C_{17}H_{17}NO \cdot HCl$ Calculated C, 70.95; H, 6.30; N, 4.87 Found C, 70.76; H, 6.30; N, 4.74

EXAMPLE 1

Ethyl 3-[N-[3-(5H-Dibenzo[a,d]cyclohepten-5-ylidene)-propyl]-N-methylamino]propionate A mixture of 2.61 g of 5-[3-(methylamino)-propylidene]-5H-dibenzo[a,d]cycloheptene, 1.20 g of ethyl acrylate, and 13 ml of ethanol was refluxed for 2 hours. After reaction was completed, the solvent was removed by distillation and the residue was purified by column chromatography on aluminum oxide [n-hexane-diethyl ether (1:1)] to give 3.22 g of slightly yellow viscous liquid.

IR spectrum $\upsilon$ (liq) cm$^{-1}$: 1736 (COO)
NMR spectrum $\delta$ (CDCl$_3$) ppm: 1.20(3H,t,J=7.0Hz), 1.96–2.81(8H,m), 2.15(3H,s), 4.11(2H,q,J=7.0Hz), 5.53(1H,t,J=7.0Hz), 6.84(2H,s), 7.23–7.42 (8H,m)

High resolution mass spectrum for $C_{24}H_{27}NO_2$ Calculated m/z: 361.2042 Found m/z: 361.1970

EXAMPLE 2

Ethyl [N-[3-(5H-Dibenzo[a,d]cyclohepten-5-ylidene)propyl]-N-methylamino]acetate

A mixture of 2.61 g of 5-[3-(methylamino)-propylidene]-5H-dibenzo[a,d]cycloheptene, 2.00 g of ethyl bromoacetate, 1.38 g of potassium carbonate, and 13 ml of N,N-dimethylformamide was stirred at 70° C. for 4 hours. After the reaction was completed, water was added to the reaction mixture and the mixture was then extracted with diethyl ether. The ether layer was washed with water and dried, and then the solvent was removed by distillation. The residue was purified by column chromatography on aluminum oxide [n-hexane-diethyl ether (1:1)] to give 1.88 g of slightly yellow viscous liquid.

IR spectrum $\upsilon$ (liq) cm$^{-1}$: 1734 (COO)
NMR spectrum $\delta$ (CDCl$_3$) ppm: 1.19(3H,t,J=7.0Hz), 1.98–2.73(4H,m), 2.28(3H,s), 3.16(2H,s), 4.13(2H,q,J=7.0Hz), 5.56(1H,t,J=7.0Hz), 6.85(2H,s), 7.21–7.41(8H,m)

The compounds of Examples 3 to 5, 11, and 12 were prepared in the same manner as described in Example 1 or Example 2.

EXAMPLE 3

Ethyl 4-[N-[3-(5H-Dibenzo[a,d]cyclohepten-5-ylidene)-propyl]-N-methylamino]butyrate Appearance: slightly yellow viscous liquid
IR spectrum $\upsilon$ (liq) cm$^{-1}$: 1736(COO)
NMR spectrum $\delta$ (CDCl$_3$) ppm: 1.21(3H,t,J=7.0Hz), 1.56–1.94(2H,m), 2.12(3H,s), 2.12–2.46(8H,m), 4.11(2H,q,J=7.0Hz), 5.56(1H,t,J=7.0Hz), 6.85(2H,s), 7.21–7.38(8H,m)

High resolution mass spectrum for $C_{25}H_{29}NO_2$ Calculated m/z: 375.2198 Found m/z: 375.2175

EXAMPLE 4

Ethyl 5-[N-[3-(5H-Dibenzo[a,d]cyclohepten-5-ylidene)-propyl]-N-methylamino]valerate Appearance: slightly yellow viscous liquid
IR spectrum $\upsilon$ (liq) cm$^{-1}$: 1736(COO)
NMR spectrum $\delta$ (CDCl$_3$) ppm: 1.19(3H,t,J=7.0Hz), 1.30–1.70(4H,m), 2.07(3H,s), 2.10–2.35(8H,m), 4.10(2H,q,J=7.0Hz), 5.53(1H,t,J=7.0Hz), 6.82(2H,s), 7.19–7.37(8H,m)

High resolution mass spectrum for $C_{26}H_{31}NO_2$ Calculated m/z: 389.2355 Found m/z: 389.2323

EXAMPLE 5

Ethyl 6-[N-[3-(5H-Dibenzo[a,d]cyclohepten-5-ylidene)-propyl]-N-methylamino]hexanoate Appearance: slightly yellow viscous liquid
IR spectrum $\upsilon$ (liq) cm$^{-1}$: 1736(COO)
NMR spectrum $\delta$ (CDCl$_3$) ppm: 1.19(3H,t,J=7.0Hz), 1.20–1.85(6H,m), 2.07(3H,s), 2.10–2.40(8H,m), 4.10(2H,q,J=7.0Hz), 5.56(1H,t,J=7.0Hz), 6.81(2H,s), 7.20–7.37(8H,m)

High resolution mass spectrum for $C_{27}H_{33}NO_2$ Calculated m/z: 403.2511 Found m/z: 403.2530

By using 11-[3-(methylamino)propylidene]-6,11-dihydrodibenz[b,e]oxepin (E-isomer:Z-isomer=70:30) obtained in Reference Example 4 as starting materials, the compounds of Examples 6 to 10 were prepared in the same manner as described in Example 1 or Example 2.

EXAMPLE 6

Ethyl [N-[3-(Dibenz[b,e]oxepin-11(6H)-ylidene)propyl]-N-methylamino]acetate

Appearance: pale yellow viscous liquid
IR spectrum υ (liq) cm⁻¹: 1740(COO)
NMR spectrum δ (CDCl₃) ppm: 1.23(3H,t,J=7.0Hz), 2.27–2.73 (4H,m), 2.29(3H,s), 3.17(2H,s), 4.16(2H,q,J=7.0Hz), 5.20(2H,br-s), 6.04(1H,t,J=7.0Hz), 6.66–7.40(8H,m)

High resolution mass spectrum for $C_{22}H_{25}NO_3$ Calculated m/z: 351.1835 Found m/z: 351.1803

EXAMPLE 7

Ethyl 3-[N-[3-(Dibenz[b,e]oxepin-11(6H)-ylidene)propyl]-N-methylamino]propionate Appearance: pale yellow viscous liquid
IR spectrum υ (liq) cm⁻¹: 1738(COO)
NMR spectrum δ (CDCl₃) ppm: 1.20(3H,t,J=7.0Hz), 2.10–2.79(8H,m), 2.14(3H,s), 4.10(2H,q,J=7.0Hz), 5.23(2H,br-s), 5.93(1H,t,J=7.0Hz), 6.60–7.34(8H,m)

High resolution mass spectrum for $C_{23}H_{27}NO_3$ Calculated m/z: 365.1991 Found m/z: 365.1977

EXAMPLE 8

Ethyl 4-[N-[3-(Dibenz[b,e]oxepin-11(6H)-ylidene)propyl]-N-methylamino]butyrate

Appearance: pale yellow viscous liquid
IR spectrum υ (liq) cm⁻¹: 1736(COO)
NMR spectrum δ (CDCl₃) ppm: 1.15(3H,t,J=7.0Hz), 1.53–1.91(2H,m), 2.05–2.51(8H,m), 2.07(3H,s), 4.06(2H,q,J=7.0Hz), 5.23(2H,br-s), 6.00(1H,t,J=7.0Hz), 6.62–7.36(8H,m)

EXAMPLE 9

Ethyl 5-[N-[3-(Dibenz[b,e]oxepin-11(6H)-ylidene)propyl]-N-methylamino]valerate

Appearance: pale yellow viscous liquid
IR spectrum υ (liq) cm⁻¹: 1738(COO)
NMR spectrum δ (CDCl₃) ppm: 1.24(3H,t,J=7.0Hz), 1.36–1.76(4H,m), 2.16(3H,s), 2.20–2.63(8H,m), 4.17(2H,q,J=7.0Hz), 5.23(2H,br-s), 6.06(1H,t,J=7.0Hz), 6.69–7.46(8H,m)

EXAMPLE 10

Ethyl 6-[N-[3-(Dibenz[b,e]oxepin-11(6H)-ylidene)propyl]N-methylamino]hexanoate

Appearance: pale yellow viscous liquid
IR spectrum υ (liq) cm⁻¹: 1738(COO)
NMR spectrum δ (CDCl₃) ppm: 1.19–1.83(6H,m), 1.21(3H,t,J=7.0Hz), 2.07–2.66(8H,m), 2.13(3H,s), 4.13(2H,q,J=7.0Hz), 5.23(2H,br-s), 6.00(1H,t,J=7.0Hz), 6.66–7.10(8H,m)

High resolution mass spectrum for $C_{26}H_{33}NO_3$ Calculated m/z: 407.2461 Found m/z: 407.2482

EXAMPLE 11

Ethyl 3-[N-Methyl-N-[3-(9H-xanthen-9-ylidene)propyl]amino]propionate

Appearance: pale yellow oil
IR spectrum υ (liq) cm⁻¹: 1736
NMR spectrum δ (CDCl₃) ppm: 1.23(3H,t,J=7.5Hz), 2.31(3H,s), 2.40–2.87(8H,m), 4.12(2H,q,J=7.5Hz), 5.82–5.90(1H,m), 7.08–7.18(4H,m), 7.22–7.31(2H,m), 7.51–7.58(2H,m)

High resolution mass spectrum for $C_{22}H_{25}NO_3$ Calculated m/z: 351.1834 Found m/z: 351.1812

EXAMPLE 12

Ethyl 4-[N-Methyl-N-[3-(9H-xanthen-9-ylidene)propyl]amino]butyrate Hydrochloride Appearance: pale yellow crystals (acetone-Et₂O) mp 138°–141° C.
Analysis for $C_{23}H_{27}NO_3 \cdot HCl$ Calculated C, 68.73; H, 7.02; N, 3.48 Found C, 68.75; H, 7.04; N, 3.57

By using (E)-11-[3-(methylamino)propylidene]-6,11-dihydrodibenz[b,e]oxepin obtained in Reference Example 4 as a starting material, the compound of Example 13 was prepared in the same manner as described in Example 1.

EXAMPLE 13

(E)-Ethyl 3-[N-[3-(Dibenz[b,e]oxepin-11(6H)-ylidene)propyl]-N-methylamino]propionate Appearance: pale yellow oil
IR spectrum υ (liq) cm⁻¹: 1734
Mass spectrum m/z: 366 (M⁺+1)
NMR spectrum δ (CDCl₃) ppm: 1.21(3H,t,J=7.5Hz), 2.03–2.78(11H,m), 4.09(2H,q,J=7.5Hz), 4.81(1H,br-s), 5.52(1H,br-s), 6.00(1H,t,7.5Hz), 6.75(1H,dd,J=7.5,1.0Hz), 6.86(1H,td,J=7.5,1.0Hz), 7.11(1H,td,J=7.5, 1.0Hz), 7.22(1H,dd,J=7.5,1.0Hz), 7.22–7.40(4H,m)

EXAMPLE 14

3-[N-[3-(5H-Dibenzo[a,d]cyclohepten-5-ylidene)propyl]-N-methylamino]propionic Acid To a solution of 1.81 g of ethyl 3-[N-[3-(5H-dibenzo[a,d]cyclohepten-5-ylidene)propyl]-N-methylamino]propionate in 19 ml of methanol, 5 ml of 2N sodium hydroxide aqueous solution was added and the mixture was refluxed for 30 minutes. The solvent was removed by distillation, and then the residue was dissolved in warm water and the solution was neutralized with 2N hydrochloric acid. The crystals precipitated were collected by filtration to give 1.23 g of colorless crystals. Recrystallization from aqueous ethanol gave colorless needles, mp 119°–120° C.

Analysis for $C_{22}H_{23}NO_2$ Calculated C, 79.25; H, 6.95; N, 4.20 Found C, 79.20; H, 7.01; N, 3.98

EXAMPLE 15

4-[N-[3-(5H-Dibenzo[a,d]cyclohepten-5-ylidene)-propyl]-N-methylamino]butyric Acid To a solution of 1.88 g of ethyl 4-[N-[3-(5H-dibenzo[a,d]cyclohepten-5-ylidene)propyl]-N-methylamino]butyrate in 19 ml of methanol, 5 ml of 2N sodium hydroxide aqueous solution was added and the mixture was refluxed for 30 minutes. The solvent was removed by distillation, and after the residue was dissolved in warm water, the solution was neutralized with 2N hydrochloric acid and then extracted with chloroform. The chloroform layer was washed with water and dried, and the solvent was removed by distillation. The residue was purified by column chromatography on silica gel [chloroform-methanol (10:1)] to give 1.53 g of pale yellow viscous liquid.

IR spectrum $\upsilon$ (KBr) cm$^{-1}$: 1578 (COO$^-$)

NMR spectrum $\delta$ (CD$_3$OD) ppm: 1.50–1.89(2H,m), 2.19–3.06(8H,m), 2.49(3H,s), 5.49(1H,t,J=7Hz), 6.92(2H,s), 7.23–7.50(8H,m)

High resolution mass spectrum for C$_{23}$H$_{25}$NO$_2$ Calculated m/z: 347.1885 Found m/z: 347.1862

The compounds of Examples 16 to 25 were prepared in the same manner as described in Example 14 or Example 15.

EXAMPLE 16

[N-[3-(5H-Dibenzo[a,d]cyclohepten-5-ylidene)propyl]-N-methylamino]acetic Acid

Appearance: colorless crystals (aq. EtOH)
mp 97°–98° C.
Analysis for C$_{21}$H$_{21}$NO$_2$ Calculated C, 78.97; H, 6.63; N, 4.39 Found C, 78.82; H, 6.88; N, 4.44

EXAMPLE 17

5-[N-[3-(5H-Dibenzo[a,d]cyclohepten-5-ylidene)-propyl]-N-methylamino]valeric Acid Appearance: colorless prisms (aq. EtOH)
mp 133°–134° C.
Analysis for C$_{24}$H$_{27}$NO$_2$ Calculated C, 79.74; H, 7.53; N, 3.87 Found C, 79.55; H, 7.80; N, 3.65

EXAMPLE 18

6-[N-[3-(5H-Dibenzo[a,d]cyclohepten-5-ylidene)-propyl]-N-methylamino]hexanoic Acid Appearance: colorless crystals (aq. EtOH)
mp 129.5°–130.5° C.
Analysis for C$_{25}$H$_{29}$NO$_2$ Calculated C, 79.96; H, 7.78; N, 3.73 Found C, 80.11; H, 7.99; N, 3.96

EXAMPLE 19

[N-[3-(Dibenz[b,e]oxepin-11(6H)-ylidene)propyl]-N-methylamino]acetic Acid

Appearance: colorless viscous liquid
IR spectrum $\upsilon$ (KBr) cm$^{-1}$: 1644 (COO)
NMR spectrum $\delta$ (CD$_3$OD)) ppm: 2.37–2.91(2H,m), 2.71(3H,s), 3.10–3.56(2H,m), 3.46(2H,s), 5.23(2H,br-s), 6.00(1H,t,J=7Hz), 6.63–7.50(8H,m)

High resolution mass spectrum for C$_{20}$H$_{21}$NO$_3$ Calculated m/z: 323.1522 Found m/z: 323.1527

EXAMPLE 20

3-[N-[3-(Dibenz[b,e]oxepin-11(6H)-ylidene)propyl]-N-methylamino]propionic Acid

Appearance: pale yellow viscous liquid
IR spectrum $\upsilon$ (KBr) cm$^{-1}$: 1725, 1608 (COO)
NMR spectrum $\delta$ (CD$_3$OD)) ppm: 2.30–2.90(4H,m), 2.63(3H,s), 2.90–3.30(4H,m), 5.23(2H,br-s), 6.08(1H,t,J=7Hz), 6.69–7.56(8H,m)

High resolution mass spectrum for C$_{21}$H$_{23}$NO$_3$ Calculated m/z: 337.1678 Found m/z: 337.1740

This compound was a mixture of stereo-isomers (E, Z), and the ratio of E-isomer (retention time: 28 min.) and Z-isomer (retention time: 32 min.) was about 70:30 as measured under the following HPLC conditions:

Column: TSK gel ODS-80TM (4.6 mm $\phi \times$150 mm)
Mobile phase: 0.01M KH$_2$PO$_4$.Na$_2$HPO$_4$ buffer (pH 6.0)-MeOH (3:2)
Flow rate: 1.0 ml / min.
Detection: Ultraviolet spectometer (225 nm)

EXAMPLE 21

4-[N-[3-(Dibenz[b,e]oxepin-11(6H)-ylidene)propyl]-N-methylamino]butyric Acid

Appearance: yellow viscous liquid
IR spectrum $\upsilon$ (KBr) cm$^{-1}$: 1713, 1608 (COO)
NMR spectrum $\delta$ (CD$_3$OD)) ppm: 1.56–2.00(2H,m), 2.10–3.23(8H,m), 2.50(3H,s), 5.23(2H,br-s), 5.97(1H,t,J=7Hz), 6.64–7.54(8H,m)

High resolution mass spectrum for C$_{22}$H$_{25}$NO$_3$ Calculated m/z: 351.1834 Found m/z: 351.1818

EXAMPLE 22

5-[N-[3-(Dibenz[b,e]oxepin-11(6H)-ylidene)propyl]-N-methylamino]valeric Acid

Appearance: colorless prisms (MeOH-Et$_2$O)
mp 150°–151° C.
Analysis for C$_{23}$H$_{27}$NO$_3$ Calculated C, 75.59; H, 7.45; N, 3.83 Found C, 75.60; It, 7.43; N, 4.02

EXAMPLE 23

6-[N-[3-(Dibenz[b,e]oxepin-11(6H)-ylidene)propyl]-N-methylamino]hexanoic Acid

Appearance: colorless viscous liquid
IR spectrum $\upsilon$ (KBr) cm$^{-1}$: 1716, 1608 (COO)
NMR spectrum $\delta$ (CD$_3$OD) ppm: 1.10–1.90(6H,m), 2.00–3.25(8H,m), 2.63(3H,s), 5.23(2H,br-s), 6.02(1H,t,J=7Hz), 6.63–7.56(8H,m) High resolution mass spectrum for C$_{24}$H$_{29}$NO$_3$ Calculated m/z: 379.2148 Found m/z: 379.2146

EXAMPLE 24

3-[N-Methyl-N-[3-(9H-xanthen-9-ylidene)propyl]amino]propionic Acid

Appearance: pale yellow amorphous
IR spectrum $\upsilon$ (liq) cm$^{-1}$: 1600 (COO$^-$)
NMR spectrum $\delta$ (DMSO-D$_6$) ppm: 2.24(3H,s), 2.36(2H,t,J=7.0Hz), 2.60–2.71(4H,m), 2.68(2H,t,J=7.0Hz), 5.95–6.00(1H,m), 7.13–7.23(4H,m), 7.27–7.33(1H,m), 7.33–7.39(1H,m), 7.59–7.63(2H,m)

EXAMPLE 25

4-[N-Methyl-N-[3-(9H-xanthen-9-ylidene)propyl-amino]butyric Acid Hydrochloride

Appearance: colorless needles (iso-PrOH)
mp 185°–187° C.
Analysis for $C_{21}H_{23}NO_3 \cdot HCl$ Calculated C, 67.46; H, 6.47; N, 3.75 Found C, 67.25; H, 6.37; N, 3.73

By using the compound of Example 13 as a starting material, the compound of Example 26 was prepared in the same manner as described in Example 14.

EXAMPLE 26

(E)-3-[N-[3-(Dibenz[b,e]oxepin-11(6H)-ylidene)-propyl]-N-methylamino]propionic Acid Appearance: colorless amorphous
IR spectrum $\upsilon$ (KBr) $cm^{-1}$: 1602
Mass spectrum m/z: 338 ($M^+ +1$)
NMR spectrum $\delta$ ($CDCl_3$) ppm: 2.36(3H,s), 2.42–2.58(4H,m), 2.68– 2.89(4H,m), 4.81(1H,br-s), 5.55(1H,br-s), 5.95(1H,t,J=7.5Hz), 6.76(1H,d,J=7.5 Hz), 6.88(1H,t,J=7.5Hz), 7.13(1H,td,J=7.5,2.0Hz), 7.19(1H,dd,J=7.5,2.0Hz), 7.19–7.43(4H,m)

Purity: 96% (E-isomer:Z-isomer=96:4; HPLC analysis)

HPLC analysis was carried out under the conditions described in Example 20.

EXAMPLE 27

A tablet is prepared as described below.

| | |
|---|---|
| Compound of the present invention | 10 mg |
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 120 mg |

EXAMPLE 28

A capsule is prepared as described below.

| | |
|---|---|
| Compound of the present invention | 10 mg |
| Lactose | q.s. |
| Calcium carboxymethylcellulose | 15 mg |
| Hydroxypropylcellulose | 2 mg |
| Magnesium stearate | 2 mg |
| | 100 mg |

The above ingredients are mixed and charged into a capsule in an ordinary manner.

EXAMPLE 29

Powder is prepared as described below.

| | |
|---|---|
| Compound of the present invention | 20 mg |
| Lactose | q.s. |
| D-Mannitol | 500 mg |
| Hydroxypropylcellulose | 5 mg |
| Talc | 2 mg |
| | 1,000 mg |

EXAMPLE 30

Injection is prepared as described below.

| | |
|---|---|
| Compound of the present invention | 1 mg |
| Glucose | 50 mg |
| Hydrochloric acid | q.s. |
| Distilled water for injection | q.s. |
| | 2 ml |

EXAMPLE 31

Suppository is prepared as described below.

| | |
|---|---|
| Compound of the present invention | 5 mg |
| Hard fat | 1,295 mg |
| | 1,300 mg |

EXAMPLE 32

Plaster is prepared as described below.

| | |
|---|---|
| Compound of the present invention | 10 mg |
| Gelatin | 1100 mg |
| Polyvinylalcohol | 250 mg |
| Methylcellulose | 100 mg |
| Glycerin | 1500 mg |
| Kaolin | 850 mg |
| Sodium polyacrylate | 50 mg |
| Polybutene | 150 mg |
| Purified water | 990 mg |
| | 5,000 mg |

Industrial Applicability

The novel tricyclic compounds of the present invention represented by the above formula (I) and pharmacologically acceptable salts thereof have reduced side effects, and thus are useful as anti-histaminic and anti-allergic agents having excellent selectivity.

What is claimed is:

1. A tricyclic compound represented by the following formula:

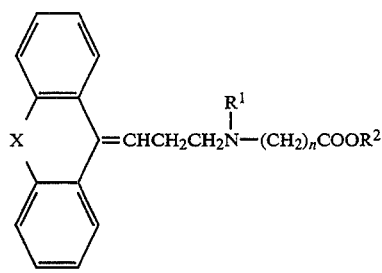

wherein
X represents $-CH_2O-$;
$R^1$ represents a lower alkyl group,
$R^2$ represents a hydrogen atom or a lower alkyl group; and
n represents an integer of from 1 to 5, and a pharmacologically acceptable salt thereof.

2. A pharmaceutical composition comprising a pharmaceutically acceptable carrier and an effective amount of a tricyclic compound represented by the following formula:

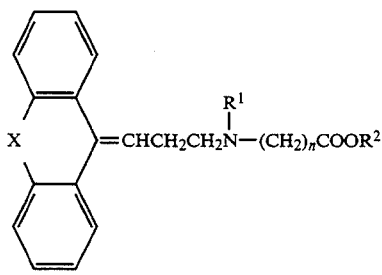

wherein

X represents —CH$_2$O—;

R$^1$ represents a lower alkyl group,

R$^2$ represents a hydrogen atom or a lower alkyl group; and n represents an integer of from 1 to 5, or a pharmacologically acceptable salt thereof.

3. The pharmaceutical composition according to claim 2 useful as an anti-histaminic agent.

4. The pharmaceutical composition according to claim 2 useful as an anti-allergic agent.

5. The pharmaceutical composition according to claim 2 useful as a medicament for the treatment of bronchial asthma.

6. A method for treating an allergic disease comprising a step of administering to a patient an effective amount of a tricyclic compound represented by the following formula:

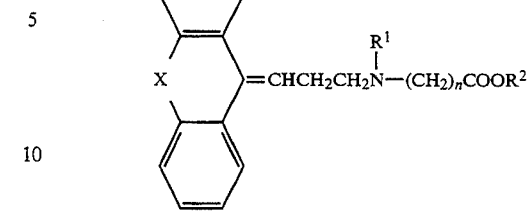

wherein

X represents —CH=CH—, —CH$_2$O—, or —O—;

R$^1$ represents a lower alkyl group,

R$^2$ represents a hydrogen atom or a lower alkyl group; and n represents an integer of from 1 to 5, or a pharmacologically acceptable salt thereof.

7. A method for treating bronchial asthma comprising a step of administering to a patient an effective amount of a tricyclic compound represented by the following formula:

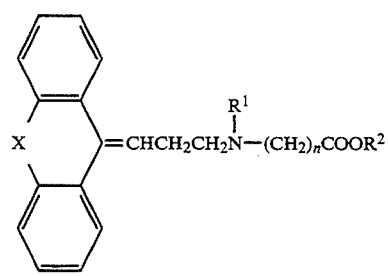

wherein

X represents —CH=CH—, —CH$_2$O—, or —O—;

R$^1$ represents a lower alkyl group,

R$^2$ represents a hydrogen atom or a lower alkyl group; and n represents an integer of from 1 to 5, or a pharmacologically acceptable salt thereof.

* * * * *